(12) United States Patent
Himmelreich et al.

(10) Patent No.: US 8,729,252 B2
(45) Date of Patent: May 20, 2014

(54) METHOD FOR FACILITATING AN AUTOMATED ISOLATION OF A BIOPOLYMER USING MAGNETIC PARTICLES

(75) Inventors: Ralf Himmelreich, Langenfeld (DE); Sabine Werner, Düsseldorf (DE)

(73) Assignee: Qiagen GmbH (DE)

(*) Notice: Subject to any disclaimer, the term of this patent is extended or adjusted under 35 U.S.C. 154(b) by 2047 days.

(21) Appl. No.: 10/567,351

(22) PCT Filed: Aug. 16, 2004

(86) PCT No.: PCT/EP2004/009156
§ 371 (c)(1), (2), (4) Date: Oct. 4, 2007

(87) PCT Pub. No.: WO2005/021748
PCT Pub. Date: Mar. 10, 2005

(65) Prior Publication Data
US 2008/0132694 A1     Jun. 5, 2008

(30) Foreign Application Priority Data

Aug. 29, 2003  (EP) .................................... 03019746

(51) Int. Cl.
*C07H 21/00* (2006.01)

(52) U.S. Cl.
USPC ................. 536/25.4; 536/25.41; 536/25.42

(58) Field of Classification Search
None
See application file for complete search history.

(56) References Cited

U.S. PATENT DOCUMENTS

| | | | |
|---|---|---|---|
| 5,705,628 A | 1/1998 | Hawkins | |
| 5,898,071 A | 4/1999 | Hawkins | |
| 6,027,945 A * | 2/2000 | Smith et al. | 436/526 |
| 6,723,510 B2 * | 4/2004 | Lubenow et al. | 435/6 |
| 6,855,499 B1 * | 2/2005 | Nargessi | 435/6 |
| 6,958,372 B2 * | 10/2005 | Parker et al. | 525/61 |
| 7,838,233 B2 * | 11/2010 | Korfhage et al. | 435/6 |

FOREIGN PATENT DOCUMENTS

| | | |
|---|---|---|
| EP | 0 757 106 A2 | 2/1997 |
| EP | 1 069 131 A1 | 1/2001 |
| EP | 1 069 131 B1 | 3/2006 |
| WO | WO 98/31840 | 7/1998 |
| WO | WO98/31840 A1 * | 7/1998 |
| WO | WO 01/70831 A1 | 9/2001 |
| WO | WO01/70831 A1 * | 9/2001 |
| WO | WO 02/09125 A1 | 1/2002 |
| WO | WO 02/066993 A1 | 8/2002 |

OTHER PUBLICATIONS

International Search Report issued in International Application No. PCT/EP2004/009156, dated Nov. 15, 2004.
SOLULINK—FAQ Database (Feb. 2011)—http://www.solulink.com/products/faqs/faqs.pdf.
Dynabeadse® for Nucleic Acid IVD—2012 Life Technologies Corporation—https://www.invitrogen.com/site/us/en/home/Products-and-Services/Applications/Diagnostics-Clinical-Research/Bead-based-IVD-Assays/Bead-based-Nucleic-Acid-IVD.html.

* cited by examiner

*Primary Examiner* — Lawrence E Crane
(74) *Attorney, Agent, or Firm* — McDermott Will & Emery LLP

(57) ABSTRACT

A method for isolating polynucleotides, such as DNA, RNA and hybrids thereof from an aqueous solution containing polynucleotides by reversibly binding the polynucleotides to silica-coated magnetic particles in the presence of a salt and non-ionic hydratable additive is disclosed. The salt and non-ionic hydratable additive concentrations are adjusted to levels that result in adhesion of the nucleic acid to the particles without degradation or precipitation of the nucleic acid.

28 Claims, No Drawings

METHOD FOR FACILITATING AN AUTOMATED ISOLATION OF A BIOPOLYMER USING MAGNETIC PARTICLES

This application is the U.S. National Phase under 35 U.S.C. §371 of International Application No. PCT/EP2004/009156, filed on Aug. 16, 2004, which in turn claims the benefit of European Application No. 03019746.1, filed on Aug. 29, 2003, the disclosures of which are incorporated by reference herein.

The present invention provides a method for isolating biopolymers, particularly nucleic acids, such as DNA or RNA or hybrid molecules of DNA and RNA, from an aqueous solution utilizing magnetic particles, particularly silica magnetic particles. The method of the present invention involves forming a complex of the magnetic particles and the biopolymer in a mixture of said particles and said aqueous solution, comprising a salt and an additive, separating the complex from the mixture by a magnetic force, and eluting the biopolymer from the complex, wherein advantageously no substantial clustering of said magnetic particles occurs during the performance of the method. In a preferred embodiment the method of the invention is performed as an automated process.

The present invention relates to methods for separating or isolating a biopolymer from an aqueous solution to produce an isolated material of sufficient purity for further processing or analysis. The present invention particularly relates to methods for separating or isolating biopolymers utilizing magnetically responsive particles capable of reversibly binding the biopolymer. The present invention more specifically relates to methods for separating or isolating biopolymers using at least one magnetically responsive particle comprising silica or a silica derivative such as silica gel which reversibly binds the biopolymer. The present invention even more specifically relates to methods for separating or isolating biopolymers as mentioned above in an automated process.

Obtaining DNA or RNA sufficiently free of contaminants for molecular biological applications is complicated by the complex systems in which the DNA or RNA is typically found. These systems, e.g. plant seed samples, leaf samples, tissue samples, cells from body fluids such as blood, lymph, milk, urine, feces, semen, or the like, cultured cells, agarose or polyacrylamide gels, or solutions in which target nucleic acid amplification has been carried out, typically include significant quantities of contaminants from which the DNA or RNA of interest must be isolated before being used in a molecular biological procedure.

Conventional protocols for obtaining DNA or RNA from cells are described in the literature (e.g. Chapter 2 (DNA) and Chapter 4 (RNA) of F. Ausubel et al., eds., Current Protocols in Molecular Biology, Wiley-Interscience, New York, 1993). Conventional DNA isolation protocols generally entail suspending the cells in a solution and using enzymes and/or chemicals, gently to lyse the cells, thereby releasing the DNA contained within the cells into the resulting lysate solution. For isolation of RNA, the conventional lysis and solubilization procedures include measures for inhibition of ribonucleases and contaminants to be separated from the RNA including DNA.

Silica materials, including glass particles, such as glass powder, silica particles, and glass microfibers prepared by grinding glass fiber filter papers, and including diatomaceous earth, have been employed in combination with aqueous solutions of chaotropic salts to separate DNA from other substances and render the DNA suitable for use in molecular biological procedures (e.g. U.S. Pat. No. 5,075,430; Marko et al., Anal. Biochem. 121, 382-387, 1982; Vogelstein et al., Proc. Natl. Acad. Sci. (USA) 76, 615-619, 1979; Boom et al., J. Clin. Microbiol. 28, 495-503, 1990; Chen and Thomas, Anal. Biochem. 101, 339-341, 1980).

Glass particles, silica particles, silica gel, and mixtures of the above have been configured in various different forms to produce matrices capable of reversibly binding nucleic acid materials when placed in contact with a medium containing such materials in the presence of chaotropic agents. Such matrices are designed to remain bound to the nucleic acid material while the matrix is exposed to an external force such as centrifugation or vacuum filtration to separate the matrix and nucleic acid material bound thereto from the remaining media components. The nucleic acid material is then eluted from the matrix by exposing the matrix to an elution solution, such as water or an elution buffer. Numerous commercial sources offer silica-based matrices designed for use in centrifugation and/or filtration isolation systems (e.g. the QiaPrep™ line of DNA isolation systems from QIAGEN, Hilden, Germany).

Magnetically responsive particles (herein referred to as 'magnetic particles') have conventionally been used to isolate and purify polypeptide molecules such as proteins or antibodies. In recent years, however, magnetic particles and methods for using magnetic particles have been developed for the isolation of nucleic acid materials. Several different types of magnetic particles designed for use in nucleic acid isolation are described in the literature, and many of those types of particles are available from commercial sources. Such magnetic particles generally fall into either of two categories, those designed to reversibly bind nucleic acid materials directly, and those designed to do so through at least one intermediary substance. The intermediary substance is referred to herein as a 'label'.

The magnetic particles designed to bind nucleic acid materials indirectly are generally used to isolate a specific nucleic acid material, such as mRNA, according to the following basic isolation procedure. First, a medium containing a nucleic acid material is placed in contact with a label capable of binding to the nucleic acid material of interest. For example, one such commonly employed label, biotinylated oligonucleotide deoxythymidine (oligo-dT), forms hydrogen bonds with the poly-adenosine tails of mRNA molecules in a medium. Each label so employed is designed to bind with a magnetically responsive particle, when placed into contact with the particle under the proper binding conditions. For example, the biotin end of a biotinylated oligo-dT/mRNA complex is capable of binding to streptavidin moieties on the surface of a streptavidin coated magnetically responsive particle. Several different commercial sources are available for streptavidin magnetic particles and reagents designed to be used in mRNA isolation using biotinylated oligo-dT as described above (e.g. the ProActive™ line of streptavidin coated microsphere particles from Bangs Laboratories, Carmel, USA).

A few types of magnetic particles have also been developed for use in the direct binding and isolation of biological materials, particularly nucleic acids. One such particle type is a magnetically responsive siliceous-oxide coated bead (e.g. MagAttract® magnetic beads, QIAGEN, Hilden, Germany; MagneSil™ magnetic beads, Promega, Madison, USA). Nucleic acids adhere to these particles in the presence of a chaotropic salt, e.g. guanidine hydrochloride or guanidine isothiocynate, alone or in combination with a binding additive like an alcohol, e.g. ethanol. After separation of the particles, desorption of the bound nucleic acids is achieved easily by incubation of the beads in a buffer with low ionic strength.

Several different methods of automated separation of magnetic beads are known from the art. The first method is to insert a magnetic or magnetizable device into the medium containing the magnetic beads, binding the magnetic beads to the magnetic or magnetizable device, and remove the magnetic or magnetizable device. In a second method the separation of medium and the magnetic particles, both aspirated into a pipette tip, is facilitated by a magnetic or magnetizable device which is brought into spatial proximity to the pipette tip. The magnetic beads are kept back in the pipette tip when the medium is removed from the pipette tip. These two methods require special technical means, e.g. a robot constructed especially for one of those methods. A more general principal in removing magnetic beads is to bring a magnetic or magnetizable device into spatial proximity to the container containing the medium and the magnetic beads. The magnetic beads bind to the container wall and the medium can be removed without carry-over of magnetic beads.

Methods as known from the art, particularly those methods using alcohols as binding additives, show the substantial disadvantage of massive clustering of the magnetic particles after binding of nucleic acids and prior to the removal of the particles. This impedes the use of such a method in an automated process due to potential physical interferences of the clustered particles with, e.g., pipette tips which may results in only partial removal of the magnetic beads from the medium and/or disturbance of subsequent automated steps.

The problem underlying the present invention is that methods as known from the art are utilizable in automated processes only on a limited scale due to the potentially massive clustering of the magnetic beads. Thus, there is need in the art to accomplish such methods capable of being automated. Therefore, the method according to this invention is of particular interest especially in high throughput analyses.

The present invention discloses a method for facilitating an automated isolation of biopolymers, particularly nucleic acids, using magnetically responsive particles capable of rapidly and efficiently binding such biopolymers, wherein no substantial clustering of the magnetic particles occurs and performance of the method in an automated process is, thus, undisturbed.

The problem is solved by utilizing certain additives at relatively low concentrations during the biopolymer isolation procedure to substantially avoid clustering of the magnetic particles.

Briefly, the present invention comprises a method for isolating a biopolymer from an aqueous solution utilizing magnet particles comprising the steps of:
 a) adding magnetic particles to an aqueous solution comprising the biopolymer of interest in the presence of a salt and an additive,
 b) incubating the aqueous solution of step a) to allow the particles of step a) and the biopolymer of step a) to form a complex,
 c) applying a magnetic field to said solution to separate the magnetic particles from said solution, and
 d) washing the separated magnetic particles of step c) under conditions in which said biopolymer is eluted from said magnetic particles,
wherein no substantial clustering of said magnetic particles occurs during the performance of the method.

In a preferred embodiment, the present invention comprises the following steps: At first, a mixture is made by adding silica magnetic particles to an aqueous solution, wherein the aqueous solution comprises a salt and an additive and the biopolymer of interest, wherein the biopolymer is DNA. The biopolymer adheres to the silica magnetic particles in the mixture. Thereafter, the silica magnetic particles are removed from the mixture utilizing an external force, most preferably using a magnetic force, and, followed by that, the biopolymer adhered to the silica magnetic particles is substantially eluted by contacting the silica magnetic particles with an elution solution.

In a further aspect, the present invention provides a kit for isolating a biopolymer from an aqueous solution, the kit comprising an aliquot of magnetic particles, preferably silica magnetic particles and most preferably siliceous-oxide coated magnetic particles, suspended in an aqueous solution in a first container. Optionally, the kit may include other components which are required to isolate a biopolymer of interest from an aqueous solution according to the present invention. Preferably, the kit comprises a chaotropic salt or a chaotropic salt solution, an additive according to the invention, and an aliquot of magnetic particles, more preferably silica magnetic particles and most preferably siliceous-oxide coated magnetic particles.

Since nucleic acids are the most preferred biopolymer isolated using the methods of the present invention, most of the detailed description of the present invention below describes this preferred aspect of the present invention. However, the detailed description of this particular aspect of the present invention is not intended to limit the scope of the invention. The present disclosure provides sufficient guidance to enable one of ordinary skill in the art of the present invention to use the methods of the present invention to isolate biopolymers other than nucleic acid materials, e.g. polypeptides, antibodies, etc.

The present invention comprises a method for isolating a biopolymer from an aqueous solution utilizing magnetic particles comprising the steps of:
 a) adding magnetic particles to an aqueous solution comprising the biopolymer of interest in the presence of a salt and an additive,
 b) incubating the aqueous solution of step a) to allow the particles of step a) and the biopolymer of step a) to form a complex,
 c) applying a magnetic field to said solution to separate the magnetic particles from said solution, and
 d) washing the separated magnetic particles of step c) under conditions in which said biopolymer is eluted from said magnetic particles,
wherein no substantial clustering of said magnetic particles occurs during the performance of the method.

An additive in terms of the present invention is a non-ionic substance which is strongly hydratable and is preferably selected from the group of ethylene glycol, tetraethylene glycol, polyalkylene glycol, cyclodextrin, carrageenan, dextran, dextran sulfate, xanthan, cellulose, hydroxypropyl cellulose, amylose, 2-Hydroxypropyl β-cyclodextrin, Agar Agar, glycerol, polyvinyl alcohol or is a mixture thereof. The above mentioned polyalkylene glycol is preferably but not restricted to polyethylene glycol, polypropylene glycol or a mixture thereof. In a more preferred embodiment of the present invention, the additive is polyethylene glycol. Surprisingly, these additives are able to inhibit substantially the clustering of the magnetic particles in an aqueous solution at relatively low concentrations which allows for a trouble-free automated process, e.g. no clogging of pipette tips due to clustered magnetic particles occurs. Therefore, the method according to this invention is of particular interest in high throughput analyses.

To solve the problem of clustering of the magnetic beads the additive is utilized at relatively low concentrations. The final concentration of the additive in step a) of the above described method is in a range of from 2% (w/v) to 7% (w/v). Preferably, the final concentration is in a range of from 3% (w/v) to 6% (w/v), more preferably in a range of from 3% (w/v) to 5% (w/v), and most preferably in a range of from 3% (w/v) to 8% (w/v).

In a preferred embodiment of the present invention, the additive is polyethylene glycol with a molecular weight in a range of from about 4000 g/mol to about 12000 g/mol, more preferably polyethylene glycol with a molecular weight in a range of from about 6000 g/mol to about 10000 g/mol, and most preferably polyethylene glycol with a molecular weight of about 8000 g/mol.

The term 'no substantial clustering' of magnetic particles as used herein means that the particles do not accumulate or stick together or adhere together in a way that the accumulated particles interfere with the present method for isolating a biopolymer due to, e.g., physical interferences of the clustered particles with, e.g., pipette tips (e.g. by clogging of the pipette tips) which may result in only partial removal of the magnetic particles from the aqueous solution and/or disturbance of subsequent steps. A cluster of magnetic particles in the terms of the present invention describes a group of accumulated magnetic particles, rather small but visible to the naked eye and, therefore, readily identifiable.

The term 'biopolymer' as used in the present invention is understood as a polynucleotide or a polypeptide, and is preferably a nucleic acid or a nucleic acid analog such as PNA or LNA, and more preferably DNA and RNA and most preferably DNA. The term nucleic acid comprises DNA or RNA or hybrid molecules of DNA and RNA. The term DNA as used in the present invention comprises but is not limited to total DNA, genomic DNA (gDNA), plasmid DNA (pDNA), DNA fragments of any length, e.g. produced from restriction enzyme digestion, amplified DNA of any length produced by an amplification reaction such as the polymerase chain reaction (PCR) or nucleic acid sequence-based amplification (NASBA), or the like, wherein the DNA may be double-stranded or single-stranded. The term RNA as used in the present invention comprises but is not limited to total RNA, mRNA, rRNA or tRNA.

The term 'magnetic particles' as used in the present invention comprises magnetically responsive particles which are able to bind biopolymers in the terms of the present invention, e.g. by ionic interaction or by ligands or by complementary sequences or the like. Such particles are well known to a person skilled in the art. The present invention is advantageously in principal independent of the kind of magnetic particles used, but preferably, the magnetic particles are silica magnetic particles and more preferably the magnetic particles are siliceous-oxide coated particles.

As used herein, the term 'magnetic' encompasses magnetic materials, such as ferromagnetic, ferrimagnetic, paramagnetic or superparamagnetic materials. These magnetic materials are part of the magnetic particles as described above and may be included in the particles by any suitable method. As mentioned above, any kind of magnetic particles are in principal suitable for the method of the present invention.

The term 'silica magnetic particles' refers to magnetic particles comprised of or coated with silica in the form of silica gel, siliceous oxide, solid silica such as glass or diatomaceous earth, or a mixture of two or more of the above. These particles are well known to the artisan.

The term 'silica gel' as used herein refers to chromatography grade silica gel, a substance which is commercially available from a number of different sources. Silica gel is most commonly prepared by acidifying a solution containing silicate, e.g. sodium silicate, to a pH of less than 10 or 11 and then allowing the acidified solution to gel (e.g. silica preparation discussion in Kurt-Othmer Encyclopedia of Chemical Technology, Vol. 6, 4th ed., Mary Howe-Grant, ed., John Wiley & Sons, pub., 1993, pp. 773-775).

The term 'glass particles' as used herein means particles of crystalline silicas (e.g., α-quartz, vitreous silica), even though crystalline silicas are not formally 'glasses' because they are not amorphous, or particles of glass made primarily of silica. Glass particles are also well known to the skilled person.

The term 'siliceous-oxide coated magnetic particles' is used herein to refer to the most preferred form of silica magnetic particles used in the present invention. The siliceous-oxide coated magnetic particles are comprised of siliceous oxide coating a core comprising at least one particle of ferrimagnetic, ferromagnetic, superparamagnetic or paramagnetic material. The siliceous-oxide coated magnetic particles used in the present invention also have an adsorptive surface of hydrous siliceous oxide. The target biopolymer, such as DNA or RNA, adheres to the adsorptive surface of the particles while other material from the source of the biopolymer, particularly deleterious contaminants such as nucleases or the like, do not adhere to or co-elute from the siliceous-oxide coated magnetic particles with the biopolymer, e.g., nucleic acids. Siliceous-oxide coated magnetic particles are well known to the artisan and are commercially available (e.g. MagAttract® magnetic beads, QIAGEN, Hilden, Germany).

The magnetic particles provided in step a) of the methods of the present invention have the capacity to form a complex with the biopolymer of interest in the aqueous solution by reversibly binding the biopolymer, e.g. by ionic interaction or by ligands or by complementary sequences or the like. The present invention may be performed using any magnetic particles possessing the property of forming a complex with the biopolymer of interest, but silica magnetic particles are preferred. Even more preferably, the method of the present invention is performed using any form of siliceous-oxide coated magnetic particles, e.g. MagAttract® magnetic beads (QIAGEN, Hilden, Germany). The silica magnetic particles used in the methods of the present invention may be any one of a number of different sizes. Smaller silica magnetic particles provide more surface area per weight unit for adsorption, but smaller particles are limited in the amount of magnetic material which can be incorporated into such particles compared to larger particles.

The term 'salt' as used herein refers to chaotropic and non-chaotropic salts. Chaotropic salts are salts of chaotropic ions according to the 'Hoffmeister-Reihe'. Such salts are highly soluble in aqueous solutions. The chaotropic ions provided by such salts, at sufficiently high concentration in aqueous solutions of proteins or nucleic acids, cause proteins to unfold, nucleic acids to lose secondary structure or, in the case of double-stranded nucleic acids, melt (i.e. strand-separation). It is thought that chaotropic ions show these effects because they disrupt hydrogen-bonding networks that exist in aqueous solutions and thereby make denatured proteins and denatured nucleic acids thermodynamically more stable than their correctly folded or structured counterparts. Chaotropic ions include guanidine, iodide, perchlorate and trichloroacetate. Preferred in the present invention is the guanidine ion. Chaotropic salts include guanidine isothiocyanate, guanidine thiocyanate, guanidine hydrochloride, sodium iodide, potassium iodide, lithium chloride, sodium perchlorate and/or sodium trichloroacetate. Preferred in the present invention are the guanidine salts, i.e. guanidine isothiocyanate, guanidine thiocyanate, guanidine hydrochloride or mixtures thereof. Non-chaotropic salts are salts of non-chaotropic ions according to the 'Hoffmeister-Reihe'. Non-chaotropic salts according to the invention include preferably sodium chloride, potassium chloride, ammonium chloride, calcium chloride, magnesium chloride or mixtures thereof.

The salt concentration in the aqueous solution of step a) of the present invention is preferably in a range of from 0.1 M and 10 M. With any salt used in the invention, it is desirable that the concentration of the salt, in any of the solutions in which the salt is employed in performing the method of the invention, remains below the solubility of the salt in the solution under all of the conditions to which the solution is subjected in performing the method of the invention. The concentration of the salt in the mixture must be sufficiently high to cause the biopolymer to adhere to the silica magnetic particles in the mixture, but not so high as to substantially denature or to degrade the biopolymer, or to cause the biopolymer to precipitate out of the aqueous solution. Proteins and large molecules of double-stranded DNA, such as chromosomal DNA, are stable at chaotropic salt concentrations between 0.5 M and 2 M, but are known to precipitate out of solution at chaotropic salt concentrations above about 2 M (e.g. U.S. Pat. No. 5,346,994, column 2, lines 56-63). Contrastingly, RNA and smaller molecules of DNA such as plasmid DNA, restriction fragments or PCR fragments of chromosomal DNA, or single-stranded DNA remain undegraded and in solution at chaotropic salt concentrations between 2 M and 5 M, which is well known to those skilled in the art. Thus, the salt concentration in a method according to the invention is dependent on the area of application and is apparent to those skilled in the art or is readily determinable.

The present invention provides convenient and efficient means for isolating a biopolymer of interest from a variety of different media. Thereby, the medium is an aqueous solution. One aspect of the present method described briefly above, wherein magnetic force is used to remove the magnetic particles from the aqueous solution, offers significant advantages over conventional isolation methods wherein a biopolymer is reversibly bound to other silica material, e.g. a silica spin column, etc. Specifically, the magnetic removal step of the method substitutes for vacuum filtration or centrifugation steps required in conventional silica binding and elution isolation methods. Several different methods of automated separation of magnetic beads are known from the art and all are suitable in the present invention. As an example, in one method a magnetic or magnetizable device is inserted into the medium containing the magnetic beads, binding the magnetic beads to the magnetic or magnetizable device, and remove the magnetic or magnetizable device. In a second method the separation of medium and the magnetic particles, both aspirated into a pipette tip, is facilitated by a magnetic or magnetizable device which is brought into spatial proximity to the pipette tip. The magnetic beads are kept back in the pipette tip when the medium is removed from the pipette tip. These two methods require special technical means, e.g. a robot constructed especially for one of those methods. A more general principal in removing magnetic beads is to bring a magnetic or magnetizable device into spatial proximity to the container containing the medium and the magnetic beads. The magnetic beads bind to the container wall and the medium can be removed without carry-over of magnetic beads.

A preferred aspect of the present invention is the facilitation of automation of isolation of a biopolymer of interest from a variety of different aqueous solutions. Methods as known from the state of the art, particularly those methods using alcohols as binding additives, show the substantial disadvantage of massive clustering of the magnetic particles prior to the removal of the particles, especially when gDNA is adhered to the particles. This impedes the use of such a method in an automated process due to potential physical interferences of the clustered particles with, e.g., pipette tips which may result in clogging of the tips and/or only partial removal of aqueous solution after magnetic separation of the magnetic particles from the aqueous solution and/or disturbance of subsequent automated steps. For example, isolation of nucleic acids from a aqueous solution in an automated process, e.g. using a BioRobot® 3000 (QIAGEN, Hilden, Germany), is often disturbed due to complications in handling of the clustered beads. The utilization of additives in terms of the present invention in relatively low concentrations surprisingly inhibits substantially the clustering of the particles and allows for the automation of the process without physical interferences as mentioned above. Therefore, the method according to this invention is of particular interest in high throughput analyses.

The biopolymer isolated using the method of the present invention may be obtained from eukaryotic or prokaryotic cells in culture or from cells taken or obtained from tissues, multicellular organisms including animals and plants; body fluids such as blood, lymph, urine, feces, or semen; embryos or fetuses; food stuffs; cosmetics; or any other source of cells. Some biopolymers, such as certain species of DNA or RNA are isolated according to the present method from the DNA or RNA of organelles, viruses, phages, plasmids, viroids or the like that infect cells. Cells will be lysed and the lysate usually processed in various ways familiar to those skilled in the art to obtain an aqueous solution of DNA or RNA, to which the separation or isolation methods of the invention are applied. The DNA or RNA, in such a solution, will typically be found with other components, such as proteins, RNA (in the case of DNA separation), DNA (in the case of RNA separation), or other types of components.

Regardless of the nature of the source of the biopolymer, the biopolymer to be isolated with the method of the present invention is provided in an aqueous solution comprising the biopolymer and molecules different from the biopolymers, e.g. cell debris, polypeptides, etc. The biopolymer must be present in the aqueous solution in a form in which it is available to adhere to the silica magnetic particles in the first step of the method. When the nucleic acid material is contained inside a cell, the cell walls or cell membrane can make the material unavailable for adhesion to the particles. Even if such cells are lysed or sufficiently disrupted to cause the nucleic acid material contained therein to be released into the surrounding solution, cellular debris in the solution could interfere with the adhesion of the nucleic acid material to the silica magnetic particles. Therefore, in cases where the nucleic acid material to be isolated using the methods of the present invention is contained within a cell, the cell is preferably first processed by lysing or disrupting the cell to produce a lysate (herein referred to as 'crude lysate'), and more preferably additionally processed by clearing the lysate of cellular debris (e.g. by centrifugation or vacuum filtration).

Any one of a number of different known methods for lysing or disrupting cells to release nucleic acid materials contained therein are suitable for use in producing a aqueous solution from cells for use in the present invention. The method chosen to release the nucleic acid material from a cell will depend upon the nature of the cell containing the material. For example, in order to cause a cell with a relatively hard cell wall, such as a fungus cell or a plant cell, to release the nucleic acid material contained therein one may need to use harsh treatments such as potent proteases and mechanical shearing with a bead mill or a homogenizer, or disruption with sound waves using a sonicator. Contrastingly, nucleic acid material can be readily released from cells with lipid bilayer membranes such as *E. coli* bacteria or animal blood cells merely by suspending such cells in an aqueous solution and adding a detergent to the solution.

Once the nucleic acid material is released from cells lysed or disrupted as described above, cellular debris likely to interfere with the adhesion of the nucleic acid material to magnetic particles can be removed using a number of different techniques known from the art or combination of these techniques. The crude lysate is preferably centrifuged to remove particulate cell debris. Optionally, the supernatant is subsequently further processed by adding a second solution to the supernatant which causes a precipitation of other cell constituents, e.g. polypeptides, and then removing the precipitate from the resulting solution by centrifugation.

The aqueous solution provided in step a) of the method of this invention does not have to contain nucleic acid material released directly from cells, i.e. the source of the biopolymer may also be an artificial source. The nucleic acid material can be the product of an amplification reaction, such as amplified DNA produced by the polymerase chain reaction (PCR) or nucleic acid sequence-based amplification (NASBA), or the like. The nucleic acid material can also be in the form of fragments of any length, e.g. produced from restriction enzyme digestion. The aqueous solution according to the invention may also be an aqueous solution comprising melted or enzymatically digested electrophoresis gel and nucleic acid material.

A complex of the magnetic particles and the biopolymer is formed in step c), preferably by exposing the magnetic particles to the aqueous solution containing the biopolymer under conditions designed to promote the formation of the complex by, e.g., ionic interaction or by ligands or by complementary sequences or the like. According to the invention, the complex is formed in a mixture of the magnetic particles and the solution, additionally comprising a salt and an additive.

In the present invention, the aqueous solution is incubated in step b) until at least some of the nucleic acid material is adhered to the magnetic particles to form a complex. This incubation step is carried out at a temperature of at least 0° C., preferably at least 4° C., and more preferably at least 20° C., provided that the incubation temperature is no more than 65° C. The incubation step must be carried out at a temperature below the temperature at which the magnetic particles begin to loose their capacity to reversibly bind the biopolymer of interest. The incubation step is most preferably carried out at about room temperature (i.e. at about 25° C.). The incubation is carried out over a sufficient period of time, allowing the target material to adhere adequately to the magnetic beads, i.e. at least 30 seconds.

The magnetic particles-biopolymer-complex is removed from the mixture using a magnetic force as described above. Other forms of external force in addition to the magnetic field can also be utilized to isolate the biological target substance according to the methods of the present invention after the initial removal step. Suitable additional forms of external force include, but are not limited to, gravity filtration, vacuum filtration and centrifugation.

In a preferred embodiment of the present invention, the magnetic particles-biopolymer-complex removed from the aqueous solution in step c) as described above is washed at least once prior to step d) by being rinsed in an aqueous solution, (herein referred to as 'washing buffer'). The washing buffer used in this optional additional step of the method preferably comprises an aqueous solution capable of removing contaminants (i.e. molecules different from the biopolymer of interest) from the magnetic particles. Any suitable washing buffer known from the art can be used in the present invention. The washing buffer preferably comprises a salt and a solvent or a solvent alone, wherein the solvent is preferably an alcohol. The concentration of salt in the washing buffer is sufficiently high to ensure that the biopolymer of interest, e.g. nucleic acids, is not eluted from the magnetic particles, e.g. silica magnetic particles, during the washing step(s). The washing buffer may additionally comprise an additive according to the invention, although the handling of the magnetic particles is normally unproblematic once the biopolymer of interest is bound to the magnetic particles. However, in steps following step c) of the method of the present invention, i.e. washing and eluting steps, the presence of additives according to the invention is, therefore, normally not required. The complex is preferably washed after removal from the aqueous solution in step c) by resuspending the complex in the washing buffer. The complex is preferably removed from the washing buffer after the first wash by any suitable method, preferably by a magnetic force, and is, after said first wash, more preferably washed at least once more, using fresh washing buffer for every washing step.

After that, the biopolymer, e.g. nucleic acids, is eluted from the magnetic particles by exposing the complex to an elution buffer. The elution buffer is preferably an aqueous solution of low ionic strength comprising a pH at which the biopolymer is stable and substantially intact. The low ionic strength of the preferred forms of the elution buffer described above ensures that the biopolymer is released from the magnetic particles. Suitable elution buffers will be readily apparent to one skilled in this art.

After elution of the biopolymer in step d) of the present invention, the biopolymer preferably remains in the resulting elution solution while magnetic particles are removed from the elution solution by external force, such as centrifugation or a magnetic field.

The biopolymer isolated by the method of the present invention is suitable, without further isolation or purification, for analysis or further processing by molecular biological procedures, e.g. isolated nucleic acids can be analyzed by, for example, sequencing, restriction analysis, or nucleic acid probe hybridization. Thus, the methods of the invention can be applied as part of methods, based on analysis of DNA or RNA, for, among other things, genotyping, diagnosing diseases, identifying pathogens, testing foods, cosmetics, blood or blood products, or other products for contamination by pathogens, forensic testing, paternity testing, and sex identification of fetuses or embryos.

DNA or RNA isolated by the method of the present invention may be processed by any of various exonucleases and endonucleases that catalyze reactions with DNA or RNA, respectively, and, in the case of DNA, can be digested with restriction enzymes, which cut restriction sites present in the DNA. Restriction fragments from the eluted DNA can be ligated into vectors and transformed into suitable hosts for cloning or expression. Segments of the eluted DNA or RNA can be amplified by any of the various methods known in the art for amplifying target nucleic acid segments. If eluted DNA is a plasmid or another type of autonomously replicating DNA, it can be transformed into a suitable host for cloning or for expression of genes on the DNA which are capable of being expressed in the transformed host.

The following, non-limiting examples teach some embodiments of the invention. In the examples, and elsewhere in the specification and claims, volumes and concentrations are at room temperature unless specified otherwise. Only the most preferred form of the magnetic silica particles was used in each of the examples below, i.e. siliceous-oxide coated magnetic particles. However, one skilled in the art of the present invention will be able to use the teachings of the present disclosure to select and use forms of the magnetic particles other than the siliceous-oxide coated magnetic particles whose use is illustrated in the aspects of the methods of the present invention demonstrated in the examples below.

EXAMPLE 1

Automated Isolation of Genomic DNA from Wheat Leafs

Isolation of gDNA was processed on a BioRobot® 3000 in combination with a BioRobot® RapidPlate™ (both QIAGEN, Hilden, Germany). 50 mg of wheat leaves were frozen in liquid nitrogen and homogenized in a MixerMill MM 300 (Retsch, Haan, Germany). 400 µl of buffer A (3.5 M guanidine isothiocyanate; 25 mM sodium citrate; pH 7.0) were added, thoroughly vortexed, and subsequently centrifuged at 6000×g for 5 minutes. 200 µl supernatant were transferred into a flat bottom microwell plate. 65 µl of 20% (w/v) polyethylene glycol 8000 and 20 µl MagAttract® magnetic beads (150 mg/ml; QIAGEN, Hilden, Germany) were added. The solution was mixed and incubated for 5 minutes at room temperature. Magnetic separation was applied and the supernatant was removed. Subsequently, beads were washed by resuspending in 200 µl buffer B (1.071 M guanidine hydrochloride; 107.1 mM potassium acetate; 50% (v/v) isopropanol; 100 ng/ml RNase A) followed by applying magnetic separation and removing of supernatant. The washing step as described was repeated twice with 100% ethanol. Afterwards, the beads were dried 5 minutes at room temperature. For elution of genomic DNA the beads were resuspended in 100 µl of buffer C (10 mM Tris/HCl; pH 8.5) and incubated for 5 minutes at room temperature.

6 to 10 µg of genomic DNA were separated per 50 mg of wheat leaves using this protocol. No problems regarding bead handling were observed during the process, i.e., no apparent bead clustering/aggregation was observed. In comparison, in an identical protocol with the exception of adding 225 µl 100% ethanol in place of 65 µl polyethylene glycol 8000, in 5 to 10 wells of a 96 well plate the beads aggregated and were partially sucked into the pipette tip or the beads occluded the pipette tip and subsequent automated steps were massively disturbed.

EXAMPLE 2

Automated Isolation of Genomic DNA from Conifer Needles

The isolation was processed on a BioRobot® 3000 in combination with a BioRobot® RapidPlate™ (both QIAGEN, Hilden, Germany). 2×2 cm of conifer needles were frozen in liquid nitrogen and homogenized in a MixerMill (Retsch, Haan, Germany). 400 µl of buffer D (1.4% (w/v) sodium dodecyl sulfate; 50 mM ethylene diamine tetra acetic acid (EDTA); 500 mM sodium chloride; 2% (w/v) polyvinylpyrrolidone; 100 mM sodium acetate; pH 5.5) were added, thoroughly vortexed, and subsequently centrifuged at 6000×g for 5 minutes. The further preparation of the probes was identical to the preparation described in Example 1.

No problems regarding bead handling were observed during the process, i.e. no apparent bead clustering/aggregartion was observed. In comparison, in an identical protocol with the exception of adding 225 µl 100% ethanol in place of 65 µl polyethylene glycol 8000, in 5 to 10 wells of a 96 well plate the beads aggregated and were partially sucked into the pipette tip or the beads occluded the pipette tip and subsequent automated steps were massively disturbed.

EXAMPLE 3

Isolation of Genomic DNA from Wheat Using Different Additives 30 mg of wheat leaves were homogenized as described above, wherein the added additive was not 65 µl 20% (w/v) polyethylene glycol 8000 but was 50 µl 25% (w/v) of aqueous dextran sulfate. No problems regarding bead handling were observed during the process, i.e. no apparent bead clustering/aggregation was observed.

Equal observations were made with different additives applying the same protocol. 50 µl 20% (w/v) cyclodextrin, 50 µl 20% (w/v) amylose and 50 µl 20% (w/v) cellulose were used as additives with an identical result.

The invention claimed is:

1. A method for isolating a nucleic acid from an aqueous solution utilizing magnetic particles comprising the steps of:
   a) adding silica-coated magnetic particles to an aqueous solution comprising the nucleic acid in the presence of a salt and a hydratable additive, which is selected from the group consisting of ethylene glycol, tetraethylene glycol, polyalkylene glycol, cyclodextrin, carageenan, dextran, dextran sulfate, xanthan, cellulose, hydroxypropyl cellulose, amylose, 2-hydroxypropyl-β-cyclodextrin, agar agar or a mixture thereof, wherein the concentration of the additive is in the range of from 2% (w/v) to 7% (w/v) and is selected to prevent substantial clustering of the magnetic particles during the performance of the method and wherein the concentration of the salt is sufficiently high to cause the nucleic acid to adhere to the particles but not so high as to substantially denature or degrade the nucleic acid or to cause the nucleic acid to precipitate,
   b) incubating the aqueous solution of step a) to allow the particles of step a) and the nucleic acid of step a) to adhere, reversibly bind or absorb to the particles of step (a),
   c) applying a magnetic field to said solution to separate the magnetic particles from said solution,
   d) optionally washing the separated magnetic particles of step c); and
   e) exposing the magnetic particles from step (c) or (d) to an elution buffer under conditions in which said nucleic acid is eluted from said magnetic particles.

2. A method according to claim 1, wherein the nucleic acid is DNA, RNA or hybrid molecules of RNA and DNA.

3. A method according to claim 1, wherein the silica-coated magnetic particles are siliceous-oxide coated magnetic particles.

4. A method according to claim 1, wherein the salt is a chaotropic salt.

5. A method according to claim 4, wherein the chaotropic salt is selected from the group consisting of guanidine isothiocyanate, guanidine thiocyanate, guanidine hydrochloride, sodium iodide, potassium iodide, lithium chloride, sodium perchlorate, sodium trichloroacetate and a mixture thereof.

6. A method according to claim 5, wherein the chaotropic salt is selected from the group consisting of guanidine isothiocyanate, guanidine thiocyanate, guanidine hydrochloride and a mixture thereof.

7. A method according to claim 1, wherein the salt is a non-chaotropic salt.

8. A method according to claim 7, wherein the non-chaotropic salt is selected from the group consisting of sodium chloride, potassium chloride, ammonium chloride, calcium chloride, magnesium chloride and a mixture thereof.

9. A method according to claim 1, wherein the concentration of the salt in the aqueous solution of step a) is in a range of from 0.1 M to 10 M.

10. A method according to claim 1, wherein the polyalkylene glycol is polyethylene glycol, polypropylene glycol or a mixture thereof.

11. A method according to claim 10, wherein the polyalkylene glycol is polyethylene glycol.

12. A method according to claim 11, wherein the polyethylene glycol has a molecular weight in a range of from about 4000 g/mol to about 12000 g/mol.

13. A method according to claim 12, wherein the polyethylene glycol has a molecular weight in a range of from about 6000 g/mol to about 10000 g/mol.

14. A method according to claim 13, wherein the polyethylene glycol has a molecular weight of about 8000 g/mol.

15. A method according to claim 1, wherein the concentration of the additive in the aqueous solution of step a) is in a range of from 2% (w/v) to 7% (w/v).

16. A method according to claim 15, wherein the concentration of the additive in the aqueous solution of step a) is in a range of from 3% (w/v) to 6% (w/v).

17. A method according to claim 16, wherein the concentration of the additive in the aqueous solution of step a) is in a range of from 3% (w/v) to 5% (w/v).

18. A method according to claim 17, wherein the concentration of the additive in the aqueous solution of step a) is in a range of from 3% (w/v) to 4.8% (w/v).

19. A method according to claim 1, wherein the incubation in step b) is performed at room temperature for at least 30 seconds.

20. A method according to claim 1, further comprising the step of washing said magnetic particles at least once following step c) and prior to step d), under conditions in which the nucleic acid remains in the complex formed with said magnetic particles in step b).

21. A method according to claim 1, wherein the method for isolating a nucleic acid from a solution utilizing magnetic particles is an automated process.

22. The method of claim 1 wherein the nucleic acid is DNA.

23. The method of claim 22 wherein the hydratable additive is polyethylene glycol.

24. A kit for isolating a nucleic acid from an aqueous solution comprising at least:
 a) an aliquot of silica-coated magnetic particles suspended in an aqueous solution in a first container,
 b) a hydratable additive, a stock solution of a hydratable additive or a ready-for application solution of a hydratable additive, wherein said hydratable additive is selected from the group consisting of ethylene glycol, tetraethylene glycol, polyalkylene glycol, cyclodextrin, carageenan, dextran, dextran sulfate, xanthan, cellulose, hydroxypropyl cellulose, amylose, 2-hydroxypropyl-β-cyclodextrin, agar agar and mixtures thereof, and/or
 c) a chaotropic or a non-chaotropic salt, a stock solution of a chaotropic or a non-chaotropic salt or a ready-for-application solution of a chaotropic or non-chaotropic salt.

25. The kit of claim 24, further comprising:
 a) an additive selected from the group consisting of ethylene glycol, polyalkylene glycol, cyclodextrin, carrageenan, dextran, dextran sulfate, xanthan, cellulose, hydroxypropyl cellulose, amylose, 2-hydroxypropyl-B-cyclodextrin, agar agar, glycerol, polyvinyl alcohol and a mixture thereof, and/or
 b) a chaotropic salt, a stock solution of said salt or a ready-for-application solution of said salt in a container.

26. The kit of claim 25 wherein the additive is a stock solution or a ready-for application solution.

27. The kit of claim 24, wherein the silica-coated magnetic particles are siliceous-oxide coated magnetic particles.

28. The kit of claim 24 wherein the nucleic acid is DNA.

* * * * *

UNITED STATES PATENT AND TRADEMARK OFFICE
CERTIFICATE OF CORRECTION

PATENT NO.       : 8,729,252 B2
APPLICATION NO.  : 10/567351
DATED            : May 20, 2014
INVENTOR(S)      : Himmelreich et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2257 days.

Signed and Sealed this
Twenty-ninth Day of September, 2015

Michelle K. Lee
*Director of the United States Patent and Trademark Office*